(12) United States Patent
Higuchi et al.

(10) Patent No.: US 6,956,128 B2
(45) Date of Patent: Oct. 18, 2005

(54) ZINC ACRYLATE PARTICLE COMPOSITION, METHOD FOR PRODUCTION THEREOF, AND GOLF BALL USING THE COMPOSITION

(75) Inventors: Hiroshi Higuchi, Chichibu (JP); Nobuyuki Kataoka, Chichibu (JP); Atsushi Nanba, Chichibu (JP); Keiji Kobayashi, Funabashi (JP); Manabu Hasegawa, Edogawa-ku (JP); Yoshinori Saito, Ichikawa (JP)

(73) Assignees: Bridgestone Sports Co., Ltd., Tokyo (JP); Nihon Joryu Kogyo Co., Ltd., Chiba (JP); Nippon Shokubai Co., Ltd., Osaka (JP)

( * ) Notice: Subject to any disclaimer, the term of this patent is extended or adjusted under 35 U.S.C. 154(b) by 299 days.

(21) Appl. No.: 10/269,946

(22) Filed: Oct. 15, 2002

(65) Prior Publication Data

US 2003/0120098 A1 Jun. 26, 2003

Related U.S. Application Data

(63) Continuation-in-part of application No. 10/173,420, filed on Jun. 18, 2002, now abandoned.

(30) Foreign Application Priority Data

Jun. 29, 2001 (JP) ........................................ 2001-198750

(51) Int. Cl.$^7$ ............................. C07F 3/06; A63B 37/06; C08L 9/00
(52) U.S. Cl. ......................... 556/131; 524/398; 473/372
(58) Field of Search ........................ 556/131; 524/398, 524/399; 473/372

(56) References Cited

U.S. PATENT DOCUMENTS

| | | | |
|---|---|---|---|
| 4,141,559 A | 2/1979 | Melvin et al. | |
| 4,169,599 A | 10/1979 | Fujio et al. | |
| 4,561,657 A | 12/1985 | Tominaga et al. | |
| 5,789,616 A | 8/1998 | Kobayashi et al. | |
| 6,136,906 A | * 10/2000 | Sano | |
| 6,278,010 B1 | 8/2001 | Tsou et al. | |
| 2004/0092636 A1 | * 5/2004 | Gajic et al. | ............... 524/406 |

FOREIGN PATENT DOCUMENTS

| | | |
|---|---|---|
| JP | 52-154436 | 12/1977 |
| JP | 58-14416 | 3/1983 |
| JP | 2 124 221 A | 2/1984 |
| JP | 60-92238 A | 5/1985 |
| JP | 60-92781 A | 5/1985 |
| JP | 60-94434 A | 5/1985 |
| JP | 2-218639 A | 8/1990 |
| JP | 8-196661 A | 8/1996 |
| JP | 11-9720 A | 1/1999 |

* cited by examiner

Primary Examiner—Celia Chang
(74) Attorney, Agent, or Firm—Sughrue Mion, PLLC

(57) ABSTRACT

A zinc acrylate particle composition which is substantially fine and, even when kneaded with a rubber composition, is capable of being uniformly dispersed and kneaded in a state very rarely inducing fast adhesion or agglomeration, a method for the production thereof, and a golf ball using the composition are provided. The zinc acrylate particle composition contemplated by this invention comprises zinc acrylate satisfying the conditions that the proportion accounted for by the zinc acrylate particles measuring not less than 300 μm in particle size as determined by the dry type method be not more than 20% by mass of all the particles, that the median of particle sizes as determined by the dry type method be in the range of 10–300 μm, and that the ratio of the median (A) of particle sizes as determined by the dry type method to the median (B) of particle sizes as determined by the wet type method exceed 2, and an anionic surfactant.

11 Claims, 1 Drawing Sheet

US 6,956,128 B2

ZINC ACRYLATE PARTICLE COMPOSITION, METHOD FOR PRODUCTION THEREOF, AND GOLF BALL USING THE COMPOSITION

RELATED APPLICATION

This application is a continuation-in-part of application Ser. No. 10/173,420, filed Jun. 18, 2002, now abandon.

BACKGROUND OF THE INVENTION

1. Field of the Invention

This invention relates to an improved zinc acrylate particle composition and a method for the production thereof. Particularly, this invention relates to a zinc acrylate particle composition intended to overcome various problems which arises while zinc acrylate is incorporated in a rubber composition or a synthetic resin and kneaded therewith, and to a method for the production thereof.

This invention further relates to a golf ball which contains the improved zinc acrylate particle composition of this invention as a component thereof.

2. Description of the Related Art

Zinc acrylate is a compound useful as a cross-linking agent. It is incorporated, for example, in a rubber composition with the aim of improving the vulcanizability thereof or in a synthetic resin as a modifying agent.

As a method for obtaining zinc acrylate, a method which comprises causing acrylic acid to react with a zinc compound in an organic solvent, distilling the reaction solution to expel the organic solvent therefrom, and thereafter drying the residue of distillation (JP-B-58-14,416) and a method which comprises filtering off the organic solvent from the reaction solution and thereafter drying the residue of the filtration have been well known heretofore. These methods, however, suffer the reaction product to adhere seriously to an inner wall or a stirring vane of a reaction vessel or to agglomerate into agglomerates and, therefore, induce such problems as deteriorating the workability, degrading the yield, and inflicting damage to the relevant devices in consequence of the repetition of such works.

With an object of solving these problems, numerous methods which comprise coating the surface of zinc acrylate particles by adding such a higher fatty acid as stearic acid or a zinc salt thereof have been proposed in the case of using zinc acrylate as kneaded in a rubber composition (JP-A-52-154,436, U.S. Pat. No. 4,141,599, JP-A-60-94,434, and JP-A-02-218,649).

These methods, however, necessitate in addition to the step of inducing the reaction between acrylic acid and a zinc compound a step of adding to the produced zinc acrylate such a higher fatty acid as stearic acid or a zinc salt thereof thereby coating the surface of the zinc acrylate particles and, as a result, require a device proper for the step. Further, when the zinc acrylate thus formed is to be kneaded actually with a rubber composition, it is required to be in the form of such a fine powder as of not more than 43 μm (325 mesh) in particle size. The zinc acrylate which is formed by the method as mentioned above has a larger particle size and, therefore, must be pulverized into a fine powder. This pulverization into the fine powder, however, is at a disadvantage in not only entailing huge labor but also deteriorating the working atmosphere so much as to incite hygienic problems because the zinc acrylate powder during and after the pulverization process is unusually liable to scatter and form dust. Furthermore, the zinc acrylate in the form of fine powder is at a disadvantage in adhering fast to an inner wall and stirring vane of a kneading device or agglomerating into agglomerates while the powder is being kneaded with a rubber composition and consequently deteriorating the workability and, on account of the liability of the fine powder to a non-uniform dispersion, suffering the finished product to become heterogeneous and to degrade quality as well.

In consideration of these problems, a method for producing zinc acrylate which is substantially fine and readily pulverizable into fine powder and, even when kneaded with a rubber composition, capable of being uniformly dispersed and kneaded in a state very rarely generating fast adhesion or agglomeration has been proposed in the official gazette of U.S. Pat. No. 5,789,616. This method is claimed to produce improved zinc acrylate by causing acrylic acid and a higher fatty acid of 12–30 carbon atoms to react with zinc oxide in an organic solvent while continuing dispersion of the zinc oxide in the organic solvent in the presence of an anionic surfactant. The zinc acrylate to be produced in Examples 1–4 and Comparative Example 1 cited in the official gazette, however, invariably contain particles having particle size of not less than 500 μm at ratios exceeding 20% by mass of the whole particles. Thus, they are in their unmodified form at a disadvantage in failing to be smoothly kneaded in rubber without inducing cohering agglomerates and failing to be fully satisfactorily dispersed as well.

Such zinc acrylate as is smoothly kneaded in a rubber composition and possesses fully satisfactory dispersibility as well, therefore, has not been obtained to date.

Further, even when zinc acrylate is used as a component for a rubber composition of a golf ball as proposed in the official gazette of JP-A-11-9,720, it has fallen short of possessing fully satisfactory kneading property and dispersibility.

SUMMARY OF THE INVENTION

An object of this invention, therefore, is to provide a zinc acrylate particle composition containing zinc acrylate which is substantially fine and, when kneaded with a rubber composition, is capable of being uniformly dispersed and kneaded without appreciably inducing the phenomenon of either adhesion and agglomeration.

Another object of this invention is to provide a zinc acrylate particle composition containing zinc acrylate which sparingly scatters and allows easy handling as a powder.

Still another object of this invention is to provide a method which permits the efficient production of such a zinc acrylate particle composition as mentioned above with a simple procedure.

Further, this invention is aimed at providing a golf ball which, by the incorporation therein of the zinc acrylate particle composition of this invention as a co-cross-linking agent which excels in workability, attains uniform dispersion and mixture in a rubber composition and avoids fast adhesion to a kneading device as well, attains the effective use of the function of the co-cross-linking agent and consequently incurs the dispersion of ball hardness only sparingly, and exhibits fully satisfactory resiliency and durability.

The present inventors, as a result of a diligent study pursued regarding a zinc acrylate particle composition with a view to accomplishing the objects mentioned above, have found that a zinc acrylate particle composition which comprises zinc acrylate satisfying the specific conditions, (i) that the proportion accounted for by the zinc acrylate particles measuring not less than 300 μm in particle size as determined by the dry type method be not more than 20% by mass of all the particles, (ii) that the median of particle sizes as determined by the dry type method be in the range of 10–300 μm, and (iii) that the ratio of the median (A) of particle sizes as determined by the dry type method to the median (B) of particle sizes as determined by the wet type method exceed 2 (A/B>2), and an anionic surfactant, very sparingly suffers generation of fast adhesion and agglomeration and can be uniformly dispersed and kneaded in the rubber composition, even when kneaded with a rubber composition.

The present inventors have also found that the zinc acrylate satisfying the specific conditions mentioned above can be easily and efficiently obtained by causing zinc oxide to react with acrylic acid while continuing dispersion of the zinc oxide in an organic solvent in the presence of an anionic surfactant thereby forming zinc acrylate particles, pulverizing the zinc acrylate particles particularly by the use of a swing hammer crusher, and classifying the pulverized zinc acrylate particles by passing through a screen having an aperture of not less than 0.2 mm.

Further, the present inventors have found that by having the zinc acrylate particle composition of this invention incorporated as a co-cross-linking agent in a rubber composition, it is made possible to diminish adhesion of the resultant blend to a kneading device, permit the blend to manifest excellent workability during the course of kneading, and allow the production of a golf ball revealing sparing dispersion of ball hardness and excelling in resiliency and durability.

The present invention has been perfected on the basis of the knowledge mentioned above.

Specifically, the objects mentioned above can be accomplished by a zinc acrylate particle composition containing zinc acrylate satisfying the conditions that the proportion accounted for by the zinc acrylate particles measuring not less than 300 μm in particle size as determined by the dry type method be not more than 20% by mass of all the particles, that the median of particle sizes as determined by the dry type method be in the range of 10–300 μm, and that the ratio of the median (A) of particle sizes as determined by the dry type method to the median (B) of particle sizes as determined by the wet type method exceed 2, and an anionic surfactant.

The objects can be also accomplished by a method for the production of a zinc acrylate particle composition of this invention, which comprises causing zinc oxide to react with acrylic acid while continuing dispersion of the zinc oxide in an organic solvent in the presence of an anionic surfactant thereby forming zinc acrylate particles, pulverizing the zinc acrylate particles particularly by the use of a swing hammer crusher, and classifying the pulverized zinc acrylate particles by passing through a screen having an aperture of not less than 0.2 mm.

Further, the objects can be accomplished by a golf ball which has as a component a heated molding of a rubber composition having incorporated in 100 parts by mass of a basic rubber using as a main material thereof 1,4-polybutadiene rubber containing not less than 40% of a cis form structure 10–60 parts by mass of a zinc acrylate particle composition of this invention as a co-cross-linking agent, 5–80 parts by mass of an inactive filler, and not more than 5 parts by mass of a cross-linking agent.

The zinc acrylate particle composition of this invention is characterized by comprising zinc acrylate satisfying the specific conditions, (i) that the proportion accounted for by the zinc acrylate particles measuring not less than 300 μm in particle size as determined by the dry type method be not more than 20% by mass of all the particles, (ii) that the median of particle sizes as determined by the dry type method be in the range of 10–300 μm, and (iii) that the ratio of the median (A) of particle sizes as determined by the dry type method to the median (B) of particle sizes as determined by the wet type method exceed 2 (A/B>2), and an anionic surfactant. The zinc acrylate particle composition fulfilling such specific conditions not only enjoys an advantage of not easily scattering even in the form of an aggregate and of allowing easy handling as a powder but also possesses a low electrical chargeability. When it is kneaded with a rubber composition, therefore, it can be uniformly and smoothly dispersed and kneaded in the rubber composition in a state not forming cohesive agglomerates and very sparingly inducing occurrence of fast adhesion and agglomeration.

The method for the production of the zinc acrylate particle composition of this invention is characterized by causing zinc oxide to react with acrylic acid while continuing dispersion of the zinc oxide in an organic solvent in the presence of an anionic surfactant thereby forming zinc acrylate particles, pulverizing the zinc acrylate particles particularly by the use of a swing hammer crusher, and classifying the pulverized zinc acrylate particles by passing through a screen having an aperture of not less than 0.2 mm. According to this method, the zinc acrylate particle composition of this invention can easily and efficiently obtained by a simple procedure.

Further, by having the zinc acrylate particle composition of this invention incorporated as a co-cross-linking agent in a rubber composition, the incorporated composition is enabled to exhibit an excellent workability and attain uniform dispersion and mixture in the rubber composition and the resultant blend is enabled to avoid adhering to a kneading device, make effective use of the function of the co-cross-linking agent, and permit the production of a golf ball revealing sparing dispersion of ball hardness and excelling in resiliency and durability.

The above and other objects, features, and advantages of the present invention will become clear from the following description of the preferred embodiments.

DESCRIPTION OF THE PREFERRED EMBODIMENTS

Figure 1:
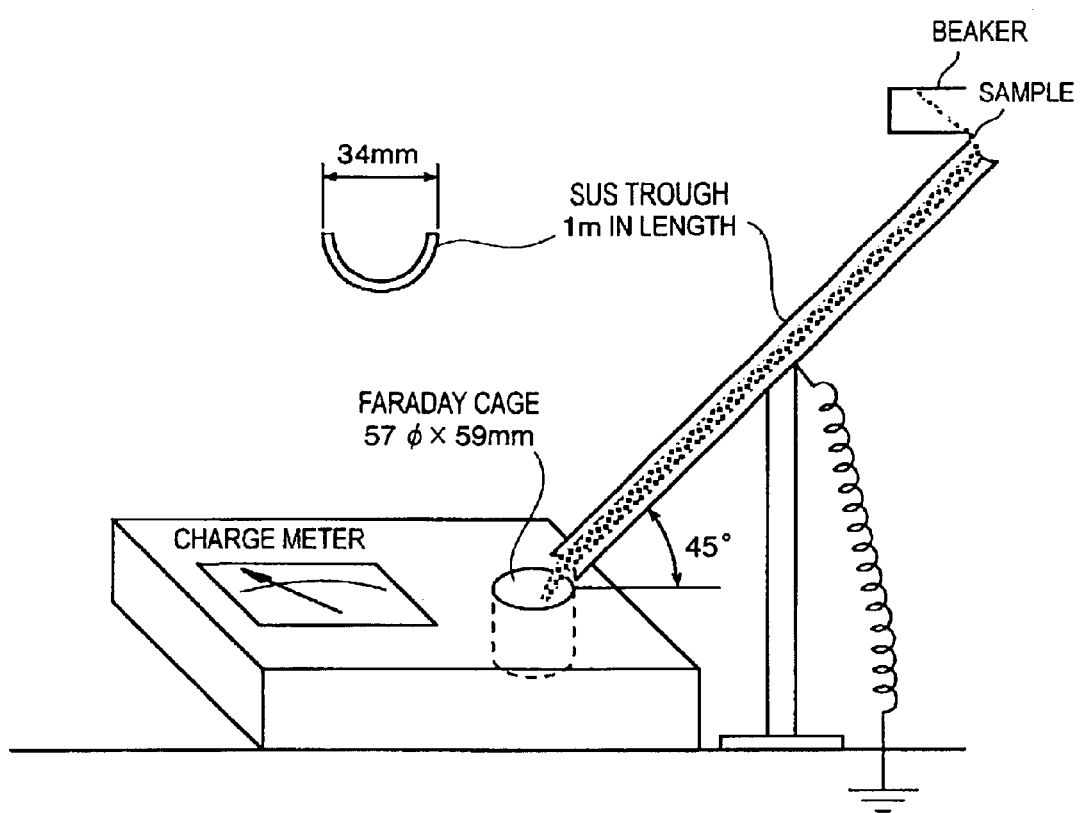
FIG. 1 is a schematic diagram of an apparatus for use in determining the electric charge stored by zinc acrylate of this invention.

Now, this invention will be described in detail below.

According to the first feature of this invention, a zinc acrylate particle composition containing zinc acrylate satisfying the conditions that the proportion accounted for by the zinc acrylate particles measuring not less than 300 μm in particle size as determined by the dry type method be not more than 20% by mass of all the particles, that the median of particle sizes as determined by the dry type method be in the range of 10–300 μm, and that the ratio of the median (A) of particle sizes as determined by the dry type method to the median (B) of particle sizes as determined by the wet type method exceed 2, and an anionic surfactant is to be provided.

The zinc acrylate particle composition of this invention contains as essential components thereof zinc acrylate satisfying the specific conditions mentioned above and an anionic surfactant. The anionic surfactant to be used as one of the raw materials for the zinc acrylate particle composition of this invention does not need to be particularly restricted but may be selected from the anionic surfactants known to the art. As typical examples of the anionic surfactant, alkylbenzene sodium sulfonate, secondary alcohol sulfosuccinic half ester salts, alkylsulfosuccinates, succinic dialkylesters of sodium sulfonates such as sodium diamylsulfosuccinate, sodium dihexylsulfosuccinate, sodium dioctylsulfosuccinate, and monoethyl monododecyl sodium sulfosuccinate, alkyl sulfates such as lauryl sulfate, tetradecyl sulfate, and oleyl sulfate, sulfuric sodium esters such as amide sulfonate and ricinoleic esters, alkyl esters of .-sulfofatty acid, esters of monosodium .-phosphorofatty acid, and sodium dialkyl phosphates may be cited. These anionic surfactants may be contained either singly or in the mixed form of two or more members. Among other anionic surfactantscited above, sodium dioctylsulfosuccinate is used particularly advantageously because it is capable of repressing such phenomena as fast adhesion, formation of cohering agglomerates, and emission of dust in the zinc acrylate in the course of production or after the production.

The zinc acrylate which constitutes the zinc acrylate particle composition of this invention satisfies the specific conditions, (i) that the proportion accounted for by the zinc acrylate particles measuring not less than 300 $\mu$m in particle size as determined by the dry type method be not more than 20% by mass of all the particles, (ii) that the median of particle sizes as determined by the dry type method be in the range of 10–300 $\mu$m, and (iii) that the ratio of the median (A) of particle sizes as determined by the dry type method to the median (B) of particle sizes as determined by the wet type method exceed 2 (A/B>2). Of these conditions, the condition of (i) consists in the fact that the proportion accounted for by the zinc acrylate particles measuring not less than 300 $\mu$m in particle size as determined by the dry type method is not more than 20% by mass, preferably not more than 15% by mass, and more preferably not more than 10% by mass of all the particles. In this invention, the lower limit of the proportion accounted for by the zinc acrylate particles measuring not less than 300 $\mu$m in particle size as determined by the dry type method may not be particularly defined because such zinc acrylate particles are preferred to be as small as possible. In consideration of the easy production, the working atmosphere, and the hygienic problems, the lower limit may be preferably 0.1% by mass and more preferably 1.0% by mass. In this case, if the proportion accounted for by the zinc acrylate particles measuring not less than 300 $\mu$m as determined by the dry type method exceeds 20% by mass, the excess would be at a disadvantage in suffering the zinc acrylate to agglomerate into agglomerates, revealing inferior workability, and failing to disperse uniformly in a rubber composition and therefore suffering the resultant product to become heterogeneous and reveal a discernible deterioration of quality.

The expression "particle size as determined by the dry type method" as used in the present specification refers to the particle size which is determined by assaying about 2 g of given zinc acrylate particles as a sample with a laser diffraction/scattering type particle size distribution tester (made by Horiba Seisakusho K.K. and marketed under the product code of "LA-920; LY-208/Dry Type Measuring Unit Specification") operated in the absence of a dispersant at a temperature of 25° C. and a humidity of 50% RH under a pressure of 3 kgf/cm$^3$ of compressed air. By this method of determination, the zinc acrylate particles can be tested for particle size.

Further, in the conditions for identifying the zinc acrylate particles as contemplated by this invention, the condition of (ii) consists in the fact that the median of particle sizes as determined by the dry type method is in the range of 10–300 $\mu$m, preferably in the range of 20–200 $\mu$m, and more preferably in the range of 30–150 $\mu$m. In this case, if the median of the diameters of zinc acrylate particles as determined by the dry type method is less than 10 $\mu$m, the shortage would be at a disadvantage in suffering the particles to acquire unduly high electric chargeability, tend to induce the formation of agglomerates, fail to be kneaded and mixed uniformly with a rubber composition, acquire no fully satisfactory dispersibility, and tend to scatter and consequently bring deterioration of the working atmosphere. Conversely, if the median of the diameters of the zinc acrylate particles as determined by the dry type method exceeds 300 $\mu$m, the excess would be likewise at a disadvantage in suffering the particles to become unduly large and consequently fail to disperse uniformly in a rubber composition.

The expression "the median (A) of the particle sizes as determined by the dry type method" as used in the present specification refers to the median radius which is determined in the same manner as described in the article "particle size as determined by the dry type method" mentioned above.

Further, in the conditions for identifying the zinc acrylate particles as contemplated by this invention, the condition of (iii) consists in the fact that the ratio of the median (A) of particle sizes as determined by the dry type method to the median (B) of particle sizes as determined by the wet type method (which is occasionally referred to simply as "A/B" in the present specification) exceeds 2 (A/B>2), preferably exceeds 2 and does not exceed 20, and more preferably falls in the range of 5–20. In this case, if the ratio A/B is not more than 2, the shortage would be at a disadvantage in suffering the particles to exhibit unduly high electric chargeability, tend to induce the formation of agglomerates, fail to be kneaded and mixed uniformly with a rubber composition, acquire no fully satisfactory dispersibility, tend to scatter, and bring the deterioration of a working atmosphere. If the ratio A/B exceeds 20, the excess would be at a disadvantage in suffering the zinc acrylate particles to agglomerate, reveal inferior workability, and fails to disperse uniformly in a rubber composition and consequently in suffering the resultant product to become heterogeneous and show a discernible deterioration of quality.

The expression "particle size as determined by the wet type method" as used in the present specification refers to the particle size determined by assaying a dispersion of given zinc acrylate particles using ISOPER H as a dispersant at a concentration thereof of about 50 mg/l with a laser diffraction/scattering type particle size distribution tester (made by Horiba Seisakusho K.K. and marketed under the product code of "LA-920; Wet Type Measuring Unit Specification") to be operated at a temperature of 25° C. and a humidity of 50% RH. By this method of determination, the fine powder of zinc acrylate can be tested for particle size. The "median (B) of particle sizes as determined by the wet type method" is expressed as the median radius which is similarly determined.

Then, the content of the zinc acrylate satisfying these conditions (i)–(iii) as contemplated by this invention does not need to be particularly restricted so long as it be incapable of affecting the occurrence of fast adhesion or agglomeration while the zinc acrylate particle composition is kneaded with a rubber composition and the uniform dispersion and kneading of the particle composition in the rubber composition. It is generally not less than 50% by mass, preferably in the range of 60–98% by mass, and more preferably in the range of 70–95% by mass. In this case, if the content of zinc acrylate is less than 50% by mass, the shortage would be at a disadvantage in allaying the characteristic properties of the zinc acrylate and preventing the rubber composition from acquiring proper hardness.

The ratio of the zinc acrylate to the anionic surfactant in this invention does not need to be particularly restricted so long as it be incapable of affecting the occurrence of fast adhesion or agglomeration while the zinc acrylate particle composition is kneaded with a rubber composition and the uniform dispersion and kneading of the particle composition in the rubber composition. It cannot be particularly restricted because it is variable with the kinds of zinc acrylate and anionic surfactant and the use for which the product is intended. The content of the anionic surfactant, for example, may be such as to fall in the range of 0.01–5 parts by mass, preferably in the range of 0.01–2 parts by mass, based on 100 parts by mass of the zinc acrylate particle composition. In this case, if the content of the anionic surfactant exceeds 5 parts by mass, the excess would be at a disadvantage in degrading the hardness and the resiliency of the produced rubber composition despite the possibility of improving the dispersibility of the particle composition. Conversely, if the content of the anionic surfactant is less than 0.01 part by mass, the shortage would bring about the possibility that the workability of the particle composition and the dispersibility thereof in a rubber composition may not be improved.

In this invention, the zinc acrylate particle composition must contain zinc acrylate and an anionic surfactant as essential components thereof. It is, however, allowed to contain other component(s). The other component which can be added in this case does not need to be particularly restricted and may be varied with the use for which the product is intended and the method for the production of the zinc acrylate particle composition. As typical examples of the other component, such higher fatty acids as stearic acid, and zinc salts thereof, and zinc oxide may be cited. In this case, the content of the other component may be varied with the kind of the other component, the use for which the product is intended, and the method for the production of the zinc acrylate particle composition and may be properly set without departing from the concept of this invention. To be specific, the content of the other component may be generally in the range of 2–40% by mass, preferably in the range of 5–30% by mass, based on the zinc acrylate particle composition.

The production of the zinc acrylate particle composition conforming to the first feature of this invention does not need to be particularly restricted but may be effected by any of the methods known to the art or by a combination of two or more such methods. It has been ascertained to the present inventors, however, that the zinc acrylate particle composition contemplated by this invention can be easily and efficiently obtained by causing zinc oxide to react with acrylic acid while continuing dispersion of the zinc oxide in an organic solvent in the presence of an anionic surfactant thereby forming zinc acrylate particles, pulverizing the zinc acrylate particles particularly by the use of a swing hammer crusher, and classifying the pulverized zinc acrylate particles by passing through a screen having an aperture of not less than 0.2 mm.

According to the second feature of this invention, therefore, a method for the production of a zinc acrylate particle composition of this invention which comprises causing zinc oxide to react with acrylic acid while continuing dispersion of the zinc oxide in an organic solvent in the presence of an anionic surfactant thereby forming zinc acrylate particles, pulverizing the zinc acrylate particles particularly by the use of a swing hammer crusher, and classifying the pulverized zinc acrylate particles by passing through a screen having an aperture of not less than 0.2 mm.

The method of this invention embraces a step of obtaining zinc acrylate particles as the raw material for the composition by causing zinc oxide to react with acrylic acid while continuing dispersion of the zinc oxide in an organic solvent in the presence of an anionic surfactant. Since this step essentially requires a step of performing the reaction of zinc oxide with acrylic acid in the presence of an anionic surfactant, the reaction product consequently formed may contain the anionic surfactant in addition to the zinc acrylate particles to be pulverized in the subsequent step. Now, one preferred embodiment concerning the production of the zinc acrylate particles contemplated by this invention will be described below. It should be noted, however, that this invention is not limited to the following embodiments.

To be more specific, according to the method of this invention, the zinc acrylate particles may be obtained by causing zinc oxide to react with acrylic acid and preferably a higher fatty acid of 12–30 carbon atoms while dispersing the zinc oxide in an organic solvent in the presence of an anionic surfactant. More preferably, in a reaction vessel provided with a stirring device possessed of a fully satisfactory stirring ability and a heating-cooling device, prescribed amounts of the organic solvent and the anionic surfactant are placed and then the zinc oxide subsequently is placed there to with stirred to prepare a suspension. Then, this suspension is maintained at a temperature in the range of 10–70° C., preferably in the range of 30–50° C. and the higher fatty acid is added thereto and made to react therewith to give rise to a higher fatty acid salt of zinc. In this case, the time for the addition and that for the reaction of the higher fatty acid may be properly selected in the range of 0.5–10 hours, preferably in the range of 1–5 hours, depending on the reaction temperature. Then, while this reaction solution is maintained, when necessary by cooling, in the range of 10–70° C., preferably in the range of 15–50° C., the acrylic acid is added thereto and made to react therewith to form zinc acrylate. Again in this case, the time for the addition and that for the reaction of the acrylic acid may be properly selected in the range of 0.5–10 hours, preferably in the range of 2–7 hours, depending on the reaction temperature.

In this invention, the zinc oxide may be used in the form of either a solid or a solution. Generally, it is preferably used in the form of a powdery solid. While the zinc oxide is preferred to have high purity, it may contain zinc hydroxide as an impurity. Although the amount of the zinc oxide to be used stoichiometrically equals the total amount of the acrylic acid and the higher fatty acid, it suffices to adjust the amounts of the acrylic acid and the higher fatty acid to be used so that the content of zinc acrylate may fall in the range of 60–98% by mass, preferably in the range of 70–95% by mass. When the zinc oxide is used as a mass adjusting agent as when the zinc acrylate particle composition is used as a core for a solid golf fall, for example, the use of the zinc oxide in an excess amount may be permitted so long as the excess induces no hindrance. When the acrylic acid is used in an excess amount, the excess acrylic acid may be expelled by distillation together with the organic solvent and the water produced by the chemical reaction and dried during the process of separating and recovering the zinc acrylate.

The acrylic acid to be used in this invention may be put to use in any of the conceivable forms and may contain a small amount of water. Preferably, however, the acrylic acid is not diluted with water. Further, the acrylic acid may contain therein such a polymerization inhibitor as hydroquinone or hydroquinone monomethyl ether. The amount of the acrylic acid to be used is not particularly restricted but is only required to be enough for the acrylic acid to react fully satisfactorily with zinc oxide. It may be generally in the range of 50–250 parts by mass, preferably in the range of 50–200 parts by mass, based on 100 parts by mass of zinc oxide.

As typical examples of the higher fatty acid of 12–30 carbon atoms which is used favorably in this invention, lauric acid, myristic acid, palmitic acid, stearic acid, behenic acid, oleic acid, and linolic acid maybe cited. These higher fatty acids may be used either singly or in the form of a combination of two or more members. Among other higher fatty acids mentioned above, palmitic acid and stearic acid may be favorably used. The higher fatty acid may be used in its unmodified form or after it has been dissolved in either the same organic solvent as used in the reaction or in acrylic acid. Optionally, it may be used as thermally dissolved. The amount of the higher fatty acid to be used is not particularly restricted so long that it can be reacted fully satisfactorily with zinc oxide. Though the optimum amount thereof to be added may be decided within the range fit for the purpose of use of zinc acrylate, it may be generally in the range of 4–150 parts by mass, preferably in the range of 10–100 parts by mass, based on 100 parts by mass of zinc oxide. In this case, if the amount of the higher fatty acid to be used is less than 4 parts by mass, the shortage would be at a disadvantage in suffering the zinc acrylate during the course of production or after the production to attain fast adhesion and dispersion only with difficulty. Conversely, if the amount of the higher fatty acid to be used exceeds 150 parts by mass, the excess would be likewise at a disadvantage in deteriorating the characteristic properties of the zinc acrylate.

The anionic surfactant to be used in this invention does not need to be particularly restricted but is only required to be selected from the anionic surfactants known to the art. Specifically, the same anionic surfactants as were cited above in the description of the first feature of this invention can be used.

In the method of this invention, the amount of the anionic surfactant to be used does not need to be particularly restricted but is only required to be enough for the reaction of zinc oxide with the acrylic acid and the higher fatty acid of 12–30 carbon atoms to proceed efficiently. It may be generally in the range of 0.03–15 parts by mass, preferably in the range of 0.03–6 parts by mass, based on 100 parts by mass of zinc oxide. The amount (content) of the anionic surfactant in the zinc acrylate particle composition to be obtained by using the anionic surfactant in the amount mentioned above may be in the range of 0.01–5% by mass, preferably in the range of 0.01–2% by mass, based on the amount of the zinc acrylate particle composition. Further, the anionic surfactant may be added to and mixed with the organic solvent used in the reaction.

The organic solvent to be used in this invention is not particularly restricted but is only required to be capable of dissolving the anionic surfactant. As typical examples of the organic solvent, hydrocarbon compounds such as methanol, ethanol, isopropanol, benzene, toluene, xylene, n-hexane, and cyclohexane may be cited. Among other hydrocarbon compounds cited above, benzene, toluene, xylene, n-hexane, and cyclohexane which are insoluble in water prove to be advantageous. Toluene and n-hexane which form an azeotropic mixture with water prove to be more preferable.

The zinc acrylate and the anionic surfactant which are obtained as described above may be separated and recovered by a known method such as, for example, by separating the water formed by the reaction and the organic solvent in the reaction vessel by means of filtration and drying the residue at a temperature in the range of 10–70° C. When the reaction vessel is a kneader blender provided with a stirring device fitted with scraping blades, the method which separates and recovers the zinc acrylate and the anionic surfactant by keeping the reaction solution stirred in its unmodified form and expelling by distillation the excess acrylic acid, the organic solvent, and water formed by the reaction at a temperature in the range of 10–70° C., preferably in the range of 15–50° C., optionally under a reduced pressure, and drying the residue of distillation may be employed favorably from the viewpoint of simplification of equipment. The time spent in this case for the distillation and the drying may be properly selected within the range of 1–20 hours, depending on the temperature prevailing at that time.

In the method of this invention, the zinc acrylate particles which have been obtained as described above are then subjected to the step of pulverization. In this case, the method for pulverizing the zinc acrylate particles is not particularly restricted but is only required to be capable of obtaining such zinc acrylate as possesses the specific particle size and the particle size distribution according to this invention. It is allowed to utilize such means of pulverization as by compression, impulsive force, friction, and shear and adopt a method of pulverization known to the art. As typical examples of the method of pulverization, methods of coarse crushing using a jaw crusher, a gyratory crusher, and a hammer crusher (a swing hammer crusher); methods of intermediary crushing using a roll crusher, a roller mill (a ring roller mill, a ball bearing mill, and a ball mill), an edge runner, a stamp mill, a impact type crushing device [a hammer mill (a high-speed hammer mill), a cage mill, a pin mill, a disintegrator, and a dismembrator], a cutting-shearing mill (a cutter mill and a phasor mill), a rod mill (a shaking rod mill), and an auto pulverizing device (an aerofall mill, a cascade mill, and a Hadsel mill); and (finely) pulverizing devices such as turbo type pulverizing devices (a turbo mill, a microcyclomator, and a hurricane mill), a ball mill [a pot mill, a tube mill (a compound mill and a compartment mill), a conical ball mill (a tricone mill), an ultra critical mill, a radial mill, a tower type pulverizing device (a tower mill), a vibrating ball mill (a circular vibrating mill, a spiral vibrating mill (a disk mill)), a planetary pulverizing device (a high swing ball mill and a centrifugal ball mill), and a side grinder], an impulsive grinders [a screen mill (an atomizer, a bantam mill, an ultrafine mill, a pulperizer), a centrifugal classifying mill (a supermicron mill, a fine micron mill, a criptron, an angmill)], a jet grinder, a colloid mill, and a mortar may be cited. Among other pulverizing means mentioned above, hammer crushers, particularly a swing hammer crusher, a hammer mill, particularly a high-speed hammer mill, and a bantam mill, particularly an ultrafine mill and a pulperizer may be used preferably and a swing hammer crusher, a bantam mill, and a pulperizer, and especially a swing hammer crusher, may be used more preferably in pulverizing the zinc acrylate particles.

The pulverizing conditions according to the second feature of this invention are not particularly restricted but are only required to be capable of obtaining zinc acrylate having the specific particle size and the particle size distribution contemplated by this invention. They may be properly selected, depending on the type of pulverizer to be used, the particle size of zinc acrylate particles as a raw material, and the number of hammers. In the case of a swing hammer crusher, for example, it is preferable to pulverize zinc acrylate particles by setting the rotational frequency in the range of 1,000–3,000 rpm, and more preferably in the range of 1,500–2,800 rpm and the number of hammers (including T-type hammers, plate hammers, and knife hammers) in the range of 20–60. The pulverizing time to be used in this case is not particularly restricted but is only required to be properly selected, depending on the amount of the raw material to be treated and the treating ability of the pulverizing device. It is preferably in the range of 0.01–24 hours and more preferably in the range of 0.01–8 hours. Then, in the case of a bantam mill, for example, it is preferable to pulverize the zinc acrylate particles by setting the rotational frequency in the range of 8,000–14,000 rpm and preferably in the range of 12,000–14,000 rpm and the number of hammers (including T-type hammers) in the range of 4–8. The pulverizing time in this case is not particularly restricted but is only required to be properly selected, depending on the amount of the raw material to be treated and the treating ability of the pulverizing device. It is preferably in the range of 0.01–24 hours and more preferably in the range of 0.01–8 hours. Further, in the case of a pulverizer, it is preferable to supply continuously the zinc acrylate particles by a screw feeder mechanism and then pulverize the zinc acrylate particles in a hammer mechanism, with the number of component hammers (including stirrup type hammers and knife type hammers) set in the range of 6–96 and the rotational frequency set in the range of 3,450–9,600 rpm and more preferably in the range of 4,600–6,900 rpm. By the same token, the pulverizing time in this case is not particularly restricted but is only required to be properly selected, depending on the amount of the raw material to be treated and the treating ability of the pulverizing device. It is preferably in the range of 0.01–24 hours and more preferably in the range of 0.01–8 hours.

The method contemplated by the second feature of this invention must comprise a step of passing the zinc acrylate particles pulverized as described above through a screen having an aperture of not less than 0.2 mm by way of classification. In the step of classification mentioned above, the aperture of the screen is preferably in the range of 0.2–10 mm and more preferably in the range of 0.2–2.0 mm. In this case, if the aperture of the screen is less than 0.2 mm, the shortage would be at a disadvantage in suffering the particles to become unduly small, acquire unduly high electric chargeability, consequently tend to form agglomerates, fail to knead uniformly with a rubber composition or acquire fully satisfactory dispersibility, and induce deterioration of the working atmosphere on account of the liability to scattering. Incidentally, when the aperture of the screen departs from the preferred range specified above, the zinc acrylate particles of this invention satisfying such specific conditions as described above can not be efficiently obtained.

The zinc acrylate particles produced by the method of this invention can exist in the form of aggregates of fine particles. When the zinc acrylate particles thus produced are pulverized by the method contemplated by the second feature of this invention, therefore, the zinc acrylate particles according to this invention and completely satisfying all the three conditions, (i) that the proportion accounted for by the zinc acrylate particles measuring not less than 300 μm in particle size as determined by the dry type method be not more than 20% by mass of all the particles, (ii) that the median of particle sizes as determined by the dry type method be in the range of 10–300 μm, and (iii) that the ratio of the median (A) of particle sizes as determined by the dry type method to the median (B) of particle sizes as determined by the wet type method exceed 2 (A/B>2), can be easily obtained.

The zinc acrylate particle composition of this invention is suitable as a co-cross-linking agent for a rubber composition forming various components such as, for example, solid cores of one-piece golf balls and two-piece golf balls, central cores and/or intermediate cores of three-piece and higher multi-piece solid golf balls having a multilayer core, and solid centers of golf balls containing a sphere of rolled yarn.

As a basic rubber, such natural rubber and/or synthetic rubber as has been heretofore used in solid golf balls can be used. Among other conceivable kinds of rubber, 1,4-polybutadiene rubber which possesses a cis form structure at a ratio of not less than 40% may be used advantageously. The reason for this lower limit is that a deviation therefrom compels the basic rubber to reveal an undue degradation of resilience. Further, in this invention, the proportion accounted for by the cis form structure in the 1,4-polybutadiene rubber is preferably not less than 60%, more preferably not less than 80%, and still more preferably not less than 90%, and most desirably not less than 95%. In this case, the polybutadiene may optionally incorporate therein natural rubber, polyisoprene rubber or styrene butadiene rubber, and the like.

In 100 parts by mass of the basic rubber, the zinc acrylate particle composition of this invention may be incorporated as a co-cross-linking agent in an amount of generally not less than 10 parts by mass, preferably not less than 15 parts by mass, and more preferably not less than 20 parts by mass. The upper limit of the amount may be 60 parts by mass, preferably 50 parts by mass, and more preferably 40 parts by mass. If the amount of the composition to be incorporated is unduly small, the produced golf ball would fail to acquire necessary hardness and would reveal a decline in resilience. If this amount is unduly large, the produced golf ball would become excessively hard and exert an unbearable sensation of hit upon the golfer.

The basic rubber, when necessary, is allowed to incorporate therein an organic sulfur compound and an age resistor. In 100 parts by mass of the basic rubber mentioned above, the organic sulfur compound may be incorporated in an amount of generally not less than 0.1 part by mass, preferably not less than 0.2 part by mass, and more preferably not less than 0.5 part by mass. The upper limit of this amount may 5 parts by mass, preferably 4 parts by mass, more preferably 3 parts by mass, and most preferably 2 parts by mass, based on 100 parts by mass of the basic rubber. Then, the age resistor may be incorporated in 100 parts by mass of the basic rubber mentioned above in an amount of generally not less than 0 part by mass, preferably not less than 0.05 part by mass, more preferably not less than 0.1 part by mass, and most preferably not less than 0.2 part by mass. The upper limit of this amount may be 3 parts by mass, preferably 2 parts by mass, more preferably 1 part by mass, and most preferably 0.5 part by mass, based on 100 parts by mass of the basic rubber mentioned above.

As typical examples of the inactive filler, zinc oxide, barium sulfate, silica, and calcium carbonate may be cited. Among other inactive fillers mentioned above, zinc oxide and barium sulfate may be used preferably. The amount of the inactive filler to be incorporated may be generally not less than 5 parts by mass, preferably not less than 10 parts by mass, and more preferably no less than 15 parts by mass, based on 100 parts by mass of the basic rubber. The upper limit of this amount may be 80 parts by mass, preferably 60 parts by mass, and more preferably 50 parts by mass, based on 100 parts by mass of the basic rubber.

As typical examples of the cross-linking agent, such organic peroxides as dicumyl peroxide, di-t-butyl peroxide, and 1,1-bis(t-butyl peroxy)-3,3,3-trimethyl cyclohexane may be cited. These organic peroxides may be incorporated either singly or in the form of a combination of two or more members. The amount of the cross-linking agent to be incorporated may be generally not more than 5 parts by mass, preferably not more than 4 parts by mass, and more preferably not more than 3 parts by mass, based on 100 parts by mass of the basic rubber. The lower limit of this amount may be 0.1 part by mass, preferably 0.4 part by mass, and more preferably 0.7 part by mass, based on 100 parts by mass of the basic rubber.

The rubber composition obtained by combining the components mentioned above may be kneaded by the use of a kneader or a roll and compressed or injection molded with a metal mold. The shaped mass consequently produced may be thermally cured at a temperature sufficiently high and for a period sufficiently long for enabling the cross-linking agent and the co-cross-linking agent to function as expected, specifically at a temperature in the range of 140–170° C. for a duration in the approximate range of 10–40 minutes to give rise to a finished product.

Then, when the golf ball contemplated by this invention is to be obtained as a two-piece solid golf ball or a multi-piece solid golf ball, what is generally used as a cover material for a golf ball can be used. As typical examples of this substance, thermoplastic or thermosetting polyurethane type elastomers, polyester type elastomers, and ionomer resin may be cited. These substances may be used either singly or in the form of a combination of two or more members.

The method for enclosing the core with the cover material does not need to be particularly restricted. A method which comprises a preliminary step of molding a composition of the cover material into a hemispherical half shell, wrapping a given core with two such half shells, and compression molding the resultant spherical composite at 130–170° C. for one five minutes or a method which comprises directly injection molding the composition of the cover material on the core may be used. The thickness and the hardness of the cover material may be properly set within the ranges for enabling of the objects of this invention to be fulfilled as expected.

Now, this invention will be described more specifically below with reference to examples. It should be noted, however, that this invention is not limited to the following examples.

Incidentally, the electric charge and rubber kneading property of zinc acrylate reported in the following examples were tested and evaluated as follows.

1. Electric Charge of Zinc Acrylate

In an apparatus for determining the electric charge as illustrated in FIG. 1, a sample was thrown down via the upper edge of an inclined trough (45° inclined trough made of SUS and measuring 34 mm in diameter and 1000 mm in length) and made to fall from the lower edge of the inclined trough into a Faraday cage (57 mm in diameter and 59 mm in height) of an electrostatic charge meter (made by Kasuga Denki K.K. and marketed under the product code of "KQ-431B Type") and then the scale of the electrostatic charge meter was read. At the same time, the amount of the sample dropped into the cage was measured with an electronic balance so as to allow the electric charge per unit mass (C/g=electrostatic charge/amount of sample dropped) to be calculated from the measured a mounts. In this case, the measurement was performed up to ten repetitions. The 5 stable measurements of electric charge per unit mass of the total 10 measurements were averaged to obtain the measured magnitude to be reported.

2. Rubber Kneading Property of Zinc Acrylate

In a Banbury mixer, 30 parts by mass of a given sample and 100 parts by mass of polybutadiene rubber were heated and kneaded. Then, the dispersibility of the sample in the rubber was visually evaluated (◯:Good, ΔA: Slightly inferior, x: Inferior) and the kneading time was measured.

EXAMPLE 1

A jacketed kneader having an inner volume of 5 liters was charged with 2386 g of toluene and 4.5 g of an anionic surfactant (content of active component 70% by mass; made by Kao Corporation and marketed under the trademark designation of "Pelex OT-P"). Then, the resultant mixed solution and 570 g of zinc oxide added thereto were stirred together to prepare a suspension. With the internal temperature of the kneader maintained at 40° C., a solution of 140 g of stearic acid as a higher fatty acid in 490 g of toluene was added to the resultant suspension over a period of one hour to obtain a suspension, which was then left reacting additionally for two hours.

Subsequently, after the internal temperature of the kneader had been cooled to 15° C., the suspension therein and 999 g of acrylic acid added gradually thereto over a period of three hours so as to reach 35° C. were left reacting at 40° C. for four hours. While the resultant reaction suspension was gradually heated to 50° C. under a reduced pressure so as to reach about 2666 Pa (20 Torrs), the operation of expelling by distillation and drying of the water formed by the reaction and the toluene was carried out over a period of five hours to obtain 1550 g of zinc acrylate particles containing 0.2% by mass of the anionic surfactant (based on the amount of zinc acrylate particles; which applies similarly hereinafter) and 10% by mass of zinc stearate.

Further, the zinc acrylate particles obtained as described above were pulverized with a coarse grinder (made by Hosokawa Micron K.K. and marketed under the trademark designation of "Hammer Mill H-12 Type") at a rotational frequency of 1700 rpm for two minutes. By classifying the pulverized zinc acrylate particles through a screen having an aperture of 1 mm, a zinc acrylate particle composition containing aggregates measuring not more than 1 mm in particle size was obtained.

The zinc acrylate in the zinc acrylate particle composition pulverized and classified as described above was measured for the median of particle sizes by the dry type method and the wet type method. As a result, the median of particle sizes determined by the dry type method and the median of particle sizes determined by the wet type method were found to be 94.8 $\mu$m and 5.5 $\mu$m, respectively. The zinc acrylate particles obtained in this example was consequently identified as aggregates of fine particles having an A/B ratio of 17.2. Then, the proportion accounted for by the zinc acrylate particles measuring not less than 300 $\mu$m in particle size as determined by the dry type method was found to be 6.3% by mass of all the particles.

Then, the zinc acrylate particle composition consequently obtained was tested for the electric charge, to find that the electric charge per unit mass was $1.7 \times 10^{-9}$ C/g. From this result, the zinc acrylate particle composition of this example was confirmed to have a low electric chargeability because it contained the aggregates.

Further, the zinc acrylate particle composition thus obtained was tested for the rubber kneading property, to find that the zinc acrylate particle composition of this example, though containing aggregates, could be smoothly kneaded in rubber without forming agglomerates, exhibited fully satisfactory dispersibility, and could complete the kneading in 20 minutes.

EXAMPLE 2

By repeating the procedure of Example 1 while changing the amounts of the anionic surfactant and the acrylic acid respectively to 4.6 g and 982 g and using 207 g of stearic acid as a higher fatty acid dissolved in 725 g of toluene, 1,600 g of zinc acrylate particles containing 0.2% by mass of the anionic surfactant and 14.3% by mass of zinc stearate was obtained.

Then, the zinc acrylate particles thus obtained were pulverized in the same manner as in Example 1, to obtain a zinc acrylate particle composition containing aggregates measuring not more than 1 mm in particle size.

When the zinc acrylate in the zinc acrylate particle composition which had been thus pulverized and classified was measured for the median of particle sizes by the dry type method and the wet type method, the medians of particle sizes as determined by the dry type method and the median of particle sizes determined by the wet type method were found to be 89.6 μm and 4.7 μm, respectively. Thus, the zinc acrylate particles obtained in the present example were found to be aggregates of fine particles having an A/B ratio of 19.1. The proportion accounted for by zinc acrylate particles measuring not less than 300 μm in particle size as determined by the dry type method was found to be 4.1% by mass of all the particles.

Then, the zinc acrylate particle composition consequently obtained was tested for the electric charge, to find that the electric charge per unit mass was $2.0 \times 10^{-9}$ C/g. From this result, the zinc acrylate particle composition of this example was confirmed to have a low electric chargeability.

Further, the zinc acrylate particle composition thus obtained was tested for the rubber kneading property, to find that the zinc acrylate particle composition of this example could be smoothly kneaded in rubber without forming agglomerates, exhibited fully satisfactory dispersibility, and could complete the kneading in 20 minutes.

EXAMPLE 3

By following the procedure of Example 1, 1,553 g of zinc acrylate particles containing 0.2% by mass of an anionic surfactant and 10% by mass of zinc stearate was obtained.

Then, by pulverizing the zinc acrylate particles obtained as described above in the same manner as in Example 1 and classifying the pulverized zinc acrylate particles by following the procedure of Example 1 while using a screen having an aperture of 3 mm in place of the screen having an aperture of 1 mm, a zinc acrylate particle composition containing aggregates of not more than 3 mm in particle size was obtained.

When the zinc acrylate in the zinc acrylate particle composition which had been thus pulverized and classified was measured for the median of particle sizes by the dry type method and the wet type method, the medians of particle sizes determined by the dry type method and the median of particle sizes determined by the wet type method were found to be 119.0 μm and 6.0 μm, respectively. Thus, the zinc acrylate particles obtained in the present example were found to be aggregates of fine particles having an A/B ratio of 19.8. The proportion accounted for by zinc acrylate particles measuring not less than 300 μm in particle size as determined by the dry type method was found to be 7.1% by mass of all the particles.

Then, the zinc acrylate particle composition consequently obtained was tested for the electric charge, to find that the electric charge per unit mass was $1.5 \times 10^{-9}$ C/g. From this result, the zinc acrylate particle composition of this example was confirmed to have a low electric chargeability.

Further, the zinc acrylate particle composition thus obtained was tested for the rubber kneading property, to find that the zinc acrylate particle composition of this example could be smoothly kneaded in rubber without forming agglomerates, exhibited fully satisfactory dispersibility, and could complete the kneading in 21 minutes.

EXAMPLE 4

By following the procedure of Example 1, 1551 g of zinc acrylate particles containing 0.2% by mass of an anionic surfactant and 10% by mass of zinc stearate was obtained.

Then, by pulverizing the zinc acrylate particles obtained as described above in the same manner as in Example 1 and classifying the pulverized zinc acrylate particles by following the procedure of Example 1 while using a screen having an aperture of 0.4 mm in place of the screen having an aperture of 1 mm, a zinc acrylate particle composition containing aggregates of not more than 0.4 mm in particle size was obtained.

When the zinc acrylate in the zinc acrylate particle composition which had been thus pulverized and classified was measured for the median of particle sizes by the dry type method and the wet type method, the medians of particle sizes determined by the dry type method and the median of particle sizes determined by the wet type method were found to be 42.1 μm and 4.6 μm, respectively. Thus, the zinc acrylate particles obtained in the present example were found to be aggregates of fine particles having an A/B ratio of 9.2. The proportion accounted for by zinc acrylate particles measuring not less than 300 μm in particle size as determined by the dry type method was 1.0% by mass of all the particles.

Then, the zinc acrylate particle composition consequently obtained was tested for the electric charge, to find that the electric charge per unit mass was $2.3 \times 10^{-9}$ C/g. From this result, the zinc acrylate particle composition of this example was confirmed to have a low electric chargeability.

Further, the zinc acrylate particle composition thus obtained was tested for the rubber kneading property, to find that the zinc acrylate particle composition of this example could be smoothly kneaded in rubber without forming agglomerates, exhibited fully satisfactory dispersibility, and could complete the kneading in 21 minutes.

COMPARATIVE EXAMPLE 1

In the same manner as in Example 1, 1552 g of zinc acrylate particles containing 0.2% by mass of an anionic surfactant and 10% by mass of zinc stearate were obtained.

Then, by pulverizing the zinc acrylate particles consequently obtained by following the procedure of Example 1 while omitting the use of the screen, a zinc acrylate particle composition was obtained.

When the zinc acrylate in the zinc acrylate particle composition which had been thus pulverized was measured for the median of particle sizes by the dry type method and the wet type method, the medians of particle sizes determined by the dry type method and the median of particle sizes determined by the wet type method were found to be 301.7 μm and 9.8 μm, respectively. Thus, the zinc acrylate particles obtained in this comparative example were found to be aggregates of fine particles having an A/B ratio of 30.8. The proportion accounted for by zinc acrylate particles measuring not less than 300 μm in particle size as determined by the dry type method was 19.8% by mass of all the particles.

Then, the zinc acrylate particle composition consequently obtained was tested for the electric charge, to find that the electric charge per unit mass was $1.4 \times 10^{-9}$ C/g. From this result, the zinc acrylate particle composition of this comparative example was confirmed to have a low electric chargeability similarly to those of Examples 1–4.

Further, the zinc acrylate particle composition thus obtained was tested for the rubber kneading property, to find that the zinc acrylate particle composition of this comparative example revealed slightly inferior dispersibility in rubber and completed the kneading in 29 minutes.

COMPARATIVE EXAMPLE 2

In the same manner as in Example 1, 1550 g of zinc acrylate particles containing 0.2% by mass of an anionic surfactant and 10% by mass of zinc stearate were obtained.

Then, by pulverizing the zinc acrylate particles consequently obtained with a fine pulverizing device (made by Hosokawa Micron K.K. and marketed under the trademark designation of "Bantam Mill AP-B Type") operated at a rotational frequency of 14000 rpm for 15 minutes and classifying the pulverized zinc acrylate particles with a screen having an aperture of 0.1 mm, a zinc acrylate particle composition having a particle size of not more than 0.1 mm was obtained.

When the zinc acrylate in the zinc acrylate particle composition which had been thus pulverized and classified was measured for the median of particle sizes by the dry type method and the wet type method, the medians of particle sizes determined by the dry type method and the median of particle sizes determined by the wet type method were found to be 8.1 μm 6.1 μm, respectively. Thus, the zinc acrylate particles obtained in this comparative example were found to have an A/B ratio of 1.3. The proportion accounted for by zinc acrylate particles measuring not less than 300 μm in particle size as determined by the dry type method was 0.0% by mass of all the particles.

Then, the product of fine pulverization of the zinc acrylate particle composition consequently obtained was tested for the electric charge, to find that the electric charge per unit mass was $1.6 \times 10^{-8}$ C/g. From this result, the zinc acrylate particle composition of this comparative example was confirmed to have an electric chargeability representing an increase by one order as compared with those of Examples 1–4.

Further, the finely pulverized product of the zinc acrylate particle composition thus obtained was tested for the rubber kneading property, to find that the zinc acrylate particle composition of this comparative example revealed slightly inferior dispersibility in rubber as compared with those of Examples 1–4 and completed the kneading in 28 minutes.

COMPARATIVE EXAMPLE 3

In the same manner as in Example 1, 1540 g of zinc acrylate particles containing 0.2% by mass of an anionic surfactant and 10% by mass of zinc stearate were obtained.

Then, the zinc acrylate particles consequently obtained were put to use in the subsequent experiment without being pulverized.

When the zinc acrylate in the zinc acrylate particle composition which had not been pulverized was measured for the median of particle sizes by the dry type method and the wet type method, the medians of particle sizes determined by the dry type method and the median of particle sizes determined by the wet type method were found to be 353.8 μm and 10.1 μm, respectively. Thus, the zinc acrylate particles obtained in this comparative example were found to be aggregates of fine particles having an A/B ratio of 35.0. The proportion accounted for by zinc acrylate particles measuring not less than 300 μm in particle size as determined by the dry type method was 32.0% by mass of all the particles.

Then, the zinc acrylate particle composition consequently obtained was tested for the electric charge, to find that the electric charge per unit mass was $1.3 \times 10^{-9}$ C/g. From this result, the zinc acrylate particle composition of this comparative example was confirmed to have a low electric chargeablity similarly to those of Examples 1–4.

Further, the zinc acrylate particle composition thus obtained was tested for the rubber kneading property, to find that the zinc acrylate particle composition of this comparative example revealed slightly inferior dispersibility in rubber and completed the kneading in 36 minutes.

The results of Examples 1–4 and Comparative Examples 1–3 are summarized in the following Tables 1–3.

TABLE 1

Results of measurement of particle size

| | Median of particle sizes (μm) | | | Proportion accounted for zinc acrylate particles of not less than 300 μm in particle size (% by mass) | |
| --- | --- | --- | --- | --- | --- |
| | A method*1 | B method*2 | A method/ B method | Dry type method | Wet type method |
| Example 1 | 94.8 | 5.5 | 17.2 | 6.3 | 0.0 |
| Example 2 | 89.6 | 4.7 | 19.1 | 4.1 | 0.0 |
| Example 3 | 119.0 | 6.0 | 19.8 | 7.1 | 0.0 |
| Example 4 | 42.1 | 4.6 | 9.2 | 1.0 | 0.0 |

TABLE 1-continued

Results of measurement of particle size

| | Median of particle sizes (μm) | | A method/ B method | Proportion accounted for zinc acrylate particles of not less than 300 μm in particle size (% by mass) | |
|---|---|---|---|---|---|
| | A method*1 | B method*2 | | Dry type method | Wet type method |
| Comparative Example 1 | 301.7 | 9.8 | 30.8 | 19.8 | 0.0 |
| Comparative Example 2 | 8.1 | 6.1 | 1.3 | 0.0 | 0.0 |
| Comparative Example 3 | 353.8 | 10.1 | 35.0 | 32.0 | 1.0 |

Note:
A method: Median of particle size determined by dry type method.
B method: Median of particle sizes determined by wet type method.

TABLE 2

Results of measurement of electric charge

| | Electric charge per unit (C/g) |
|---|---|
| Example 1 | θ 1.7 × 10$^{-9}$ |
| Example 2 | θ 2.0 × 10$^{-9}$ |
| Example 3 | θ 1.5 × 10$^{-9}$ |
| Example 4 | θ 2.3 × 10$^{-9}$ |
| Comparative Example 1 | θ 1.4 × 10$^{-9}$ |
| Comparative Example 2 | θ 1.6 × 10$^{-8}$ |
| Comparative Example 3 | θ 1.3 × 10$^{-9}$ |

TABLE 3

Results of rubber kneading

| | Dispersibility | Kneading time (min) |
|---|---|---|
| Example 1 | ◯ | 20 |
| Example 2 | ◯ | 20 |
| Example 3 | ◯ | 21 |
| Example 4 | ◯ | 21 |
| Comparative Example 1 | Δ | 29 |
| Comparative Example 2 | Δ | 28 |
| Comparative Example 3 | X | 36 |

Note)
◯: Satisfactory dispersibility
Δ: Slightly inferior dispersibility
X: Inferior dispersibility

EXAMPLE 5

Rubber compositions of formulations using components of varying proportions indicated in Table 4 were prepared by kneading the zinc acrylate particle compositions of Examples 1–4 and Comparative Examples 1,–3, respectively. They were compression molded each in a core grade metal mold at 155° C. for 20 minutes to obtain solid cores having a diameter of about 38.9 mm and a mass of about 36.0 g.

During the course of the kneading, the rubber compositions were tested for the adhesion to a kneading device, the core hardness after the vulcanization, and the resilience. The results are shown in Table 4. In Table 4, the core hardness is represented as the degree of deformation (mm) of a solid core under a load of 980N, and the resiliency which was measured with an initial velocity meter similar in type to the instrument of USGA, an authorized organ is represented as the difference (m/s) from the standard result of Comparative Example 1.

Then, two-piece solid golf balls having a diameter of about 42.7 mm and a mass of 45.3 g were obtained by injection molding a cover material composition formed of ionomer resin (Haimiran 1601/Haimiran/1557=50/50) on the solid cores obtained as described above. As a result, all the golf balls obtained by using the zinc acrylate particle compositions of Examples 1–4 excelled in resiliency and possessed proper ball hardness revealing no discernible dispersion.

TABLE 4

| | | | Example 1 | Example 2 | Example 3 | Example 4 | Comparative Example 2 | Comparative Example 1 | Comparative Example 3 |
|---|---|---|---|---|---|---|---|---|---|
| Formulation of solid coe | Polybutadiene | | 100 | 100 | 100 | 100 | 100 | 100 | 100 |
| | Co-cross-linking agent | Example 1 | 25 | | | | | | |
| | | Example 2 | | 25 | | | | | |
| | | Example 3 | | | 25 | | | | |
| | | Example 4 | | | | 25 | | | |
| | | Comparative Example 1 | | | | | | 25 | |

TABLE 4-continued

|  |  | Example 1 | Example 2 | Example 3 | Example 4 | Comparative Example 2 | Comparative Example 1 | Comparative Example 3 |
|---|---|---|---|---|---|---|---|---|
|  | Comparative Example 2 |  |  |  | 25 |  |  |  |
|  | Comparative Example 3 |  |  |  |  |  |  | 25 |
|  | Zinc oxide | 7 | 7 | 7 | 7 | 7 | 7 | 7 |
|  | Barium sulfate | 16 | 16 | 16 | 16 | 16 | 16 | 16 |
|  | Dicumyl peroxide | 1.4 | 1.4 | 1.4 | 1.4 | 1.4 | 1.4 | 1.4 |
| Kneading time | Dispersion during the kneading | Good | Good | Good | Good | Bad | Normal | Bad |
|  | Adhesion to kneading device | No | No | No | No | No | Adhesion | No |
| Core properties | Deformation under load of 980N (Min.–Max.) Minimum (mm) | 2.92 | 2.99 | 2.89 | 2.90 | 2.79 | 2.81 | 2.80 |
|  | Maximum (mm) | 3.16 | 3.25 | 3.15 | 3.15 | 3.18 | 3.19 | 3.25 |
|  | Resiliency (m/s) | +0.2 | +0.2 | +0.2 | +0.2 | 0 | 0 | 0 |

The entire disclosure of Japanese Patent Application No. 2001-198750 filed on Jun. 29, 2001 including specification, claims, drawings and summary are incorporated herein by reference in its entirety.

What is claimed is:

1. A zinc acrylate particle composition comprising zinc acrylate particles satisfying the conditions that the proportion accounted for by the zinc acrylate particles measuring not less than 300 μm in particle size as determined by the dry type method is not more than 20% by mass of all the zinc acrylate particles, that the median of zinc acrylate particle sizes as determined by the dry type method is in the range of 10–300 μm, and that the ratio of the median (A) of zinc acrylate particle sizes as determined by the dry type method to the median (B) of zinc acrylate particle sizes as determined by the wet type method exceed 2, and an anionic surfactant.

2. A zinc acrylate particle composition according to claim 1, wherein the proportion accounted for by zinc acrylate particles measuring not less than 300 μm as determined by the dry type method is not more than 15% by mass of all the particles.

3. A zinc acrylate particle composition according to claim 1, wherein the median of zinc acrylate particle sizes as determined by the dry method is in the range of 20–200 μm.

4. A zinc acrylate particle composition according to claim 1, wherein the ratio of the median (A) of zinc acrylate particle sizes as determined by the dry type method to the median (B) of zinc acrylate particle sizes as determined by the wet type method exceeds 2 and not exceeding 20.

5. A method for the production of a zinc acrylate particle composition set forth in claim 1, which comprises causing zinc oxide to react with acrylic acid while continuing dispersion of the zinc oxide in an organic solvent in the presence of an anionic surfactant thereby forming zinc acrylate particles, pulverizing the zinc acrylate particles, and classifying the pulverized zinc acrylate particles by passing through a screen having an aperture of not less than 0.2 mm.

6. A method according to claim 5, wherein the pulverization is carried out by the use of a swing hammer crusher.

7. A method according to claim 5, wherein the screen has an aperture in the range of 0.2–10 mm.

8. A golf ball comprising a component a heated molding of a rubber composition having incorporated in 100 parts by mass of a basic rubber using as a main material thereof 1,4-polybutadiene rubber containing not less than 40% of a cis form structure 10–60 parts by mass of zinc acrylate particle composition of claim 1 co-cross-linking agent, 5–80 parts by mass of an inactive filler, and not more than 5 parts by mass of a cross-linking agent.

9. A golf ball according to claim 8, wherein the proportion accounted for by zinc acrylate particles measuring not less than 300 μm as determined by the dry type method is not more than 15% by mass of all the zinc acrylate particles.

10. A golf ball according to claim 8, wherein the median of zinc acrylate particle sizes as determined by the dry method is in the range of 20–200 μm.

11. A golf ball according to claim 8, wherein the ratio of the median (A) of zinc acrylate particle sizes as determined by the dry type method to the median (B) of zinc acrylate particle sizes as determined by the wet type method exceeds 2 and not exceeding 20.

* * * * *